(12) United States Patent
Johnson

(10) Patent No.: US 7,649,977 B2
(45) Date of Patent: Jan. 19, 2010

(54) NEUTRON-GAMMA RAY TOMOGRAPHY

(75) Inventor: Gregory A. Johnson, Camarillo, CA (US)

(73) Assignee: Hamilton Sundstrand Corporation, Windsor Locks, CT (US)

( * ) Notice: Subject to any disclaimer, the term of this patent is extended or adjusted under 35 U.S.C. 154(b) by 217 days.

(21) Appl. No.: 11/900,646

(22) Filed: Sep. 12, 2007

(65) Prior Publication Data

US 2009/0067574 A1 Mar. 12, 2009

(51) Int. Cl.
*G01N 23/04* (2006.01)
*H01J 35/10* (2006.01)

(52) U.S. Cl. .......................................... 378/57; 378/143

(58) Field of Classification Search ............... 378/46, 378/57, 98.8, 98.9; 376/114, 116; 250/496.1
See application file for complete search history.

(56) References Cited

U.S. PATENT DOCUMENTS

| | | | |
|---|---|---|---|
| 5,838,759 A | 11/1998 | Armistead | |
| 5,930,314 A | 7/1999 | Lanza | |
| 6,205,195 B1 | 3/2001 | Lanza | |
| 6,693,281 B2 | 2/2004 | Chen et al. | |
| 6,870,894 B2 | 3/2005 | Leung et al. | |
| 6,998,617 B2 | 2/2006 | D'Emilio et al. | |
| 7,026,627 B2 | 4/2006 | Fowler, Jr. et al. | |
| 7,116,235 B2 | 10/2006 | Alioto et al. | |
| 7,151,815 B2 | 12/2006 | Ruddy et al. | |
| 7,183,554 B2 | 2/2007 | Gallagher et al. | |
| 2001/0019595 A1 | 9/2001 | Michaudon | |
| 2003/0147484 A1* | 8/2003 | Olshansky et al. | 376/157 |
| 2005/0135536 A1 | 6/2005 | Lyoussi et al. | |
| 2008/0298545 A1* | 12/2008 | Bueno et al. | 378/57 |

* cited by examiner

*Primary Examiner*—Irakli Kiknadze
(74) *Attorney, Agent, or Firm*—Kinney & Lange, P.A.

(57) ABSTRACT

A neutron-gamma ray tomography system comprises a source, a detector array, and an image processor. The source illuminates an object with a dual neutron-gamma ray beam. The detector array characterizes neutron and gamma ray attenuation in the object. The image processor generates tomography as a function of the neutron and gamma ray attenuation.

18 Claims, 5 Drawing Sheets

NEUTRON-GAMMA RAY TOMOGRAPHY

CROSS-REFERENCE TO RELATED APPLICATIONS

This application is related to co-pending U.S. patent application Ser. No. 11/900,640 by Andrew J. Zillmer, Nathan J. Hoffman and David Wait, entitled DUAL NEUTRON-GAMMA RAY SOURCE, filed on even date with this application, and is assigned to the same assignee.

This application is related to co-pending U.S. patent application Ser. No. 11/900,654 by Andrew J. Zillmer, Nathan J. Hoffman and Gregory A. Johnson, entitled VARIABLE-RATIO NEUTRON-GAMMA RAY SOURCE, filed on even date with this application, and is assigned to the same assignee.

BACKGROUND

This invention relates generally to imaging technology, and in particular to large-scale imaging systems for modular cargo containers. Specifically, the invention concerns a fast tomography system utilizing a dual neutron-gamma ray beam, and adaptable for use with a large-scale, cost-effective cargo container security program.

Increased global trade has provided substantial economic benefits to a number of world markets, but the commensurate growth in international shipping has raised significant security concerns as well. In particular, modular containers (also known as ISO containers, in reference to the International Organization for Standardization) facilitate cost-effective commerce in a wide range of products, but they also create a vulnerable intermodal shipping conduit through which contraband, weapons, and other dangerous materials can be readily transported, while remaining concealed from existing security systems.

The risk associated with special nuclear materials (SNM) is particularly acute. Special nuclear materials are fissile heavy metals including uranium (U-233 and U-235) and plutonium (particularly Pu-239, but also Pu-238 and other isotopes). Special nuclear materials can be employed in sub-critical reactions ("dirty bombs"), or, with sufficient expertise, used to create crude atomic weapons. In the worst-case scenario, a sufficient quantity of SNM could also serve as the trigger for a high-yield thermonuclear device.

The essential problem is that the quantity of SNM required to pose a strategic risk is quite small, particularly on the scale of a typical ISO container. Specifically, a type I or "strategic" mass of SNM is defined by formula quantity $M_f$ in excess of five kilograms (5 kg), where the formula quantity is $$M_f = m_{U\text{-}235} + 2.5 \times (m_{U\text{-}233} + m_{Pu}). \tag{1}$$

Variables $m_{U\text{-}233}$, $m_{U\text{-}235}$, and $m_{Pu}$ are the masses of uranium-233, uranium-235 and plutonium, respectively, with a two-point-five multiplier on the latter two. Thus a strategic quantity of U-235 is only five kilograms (5 kg), or about the size of a grapefruit. For U-233 and plutonium, only 2 kg is required.

A standard ISO container is eight feet wide (2.44 m), nine feet high (2.59 m) and twenty to forty feet long (6.10 m-12.20 m), with a capacity of twenty tons or more (21,600 kg-26,500 kg). This provides ample volume to conceal strategic quantities of SNM, and to shield them from standard inspection programs. To be effective, therefore, new technologies must provide detailed imaging on an extremely large scale, and must also be fast, efficient and cost-effective enough to handle intermodal traffic measured in the millions of units per month.

Prior art systems have approached this problem via both passive and active detector technologies. Passive detectors search for the characteristic radiation emitted by special nuclear materials, which are radioactive. Because a typical ISO container is so large compared to the type-I mass, however, strategic SNM quantities can be relatively easily shielded, reducing external emissions to a level at which many passive systems become ineffective.

Active systems employ X-ray transmission radiography and other imaging techniques, and are effective at detecting both SNM and associated shielding. Unfortunately, only the highest energy X-rays are sufficiently penetrating for use on a typical ISO container, and at high energy X-rays suffer from low resolution, slow imaging times, and the need for extensive human operator interpretation.

As a result, the majority of ISO container traffic is not subject to effective security screening. There remains, therefore, a need for fast imaging and detection techniques that combine penetrating radiation systems with advance image processing, and are adaptable to a large-scale, cost-effective cargo container security program.

SUMMARY

This invention concerns a fast tomography system for large-scale cargo container security inspections. The system comprises a neutron-gamma ray source, a detector array, and an image processor. The source interrogates a cargo container or illuminates an object with a dual neutron-gamma ray beam. The detector array detects neutron and gamma ray transmission through the object or container, characterizing neutron and gamma ray attenuation within it. The image processor generates three-dimensional computer-assisted tomography (CAT) images as a function of the transmission and attenuation. Specifically, the images are generated as a function of independent neutron and gamma ray attenuation coefficients, which are characterized by the transmitted intensities of each beam component.

DETAILED DESCRIPTION

Figure 1:
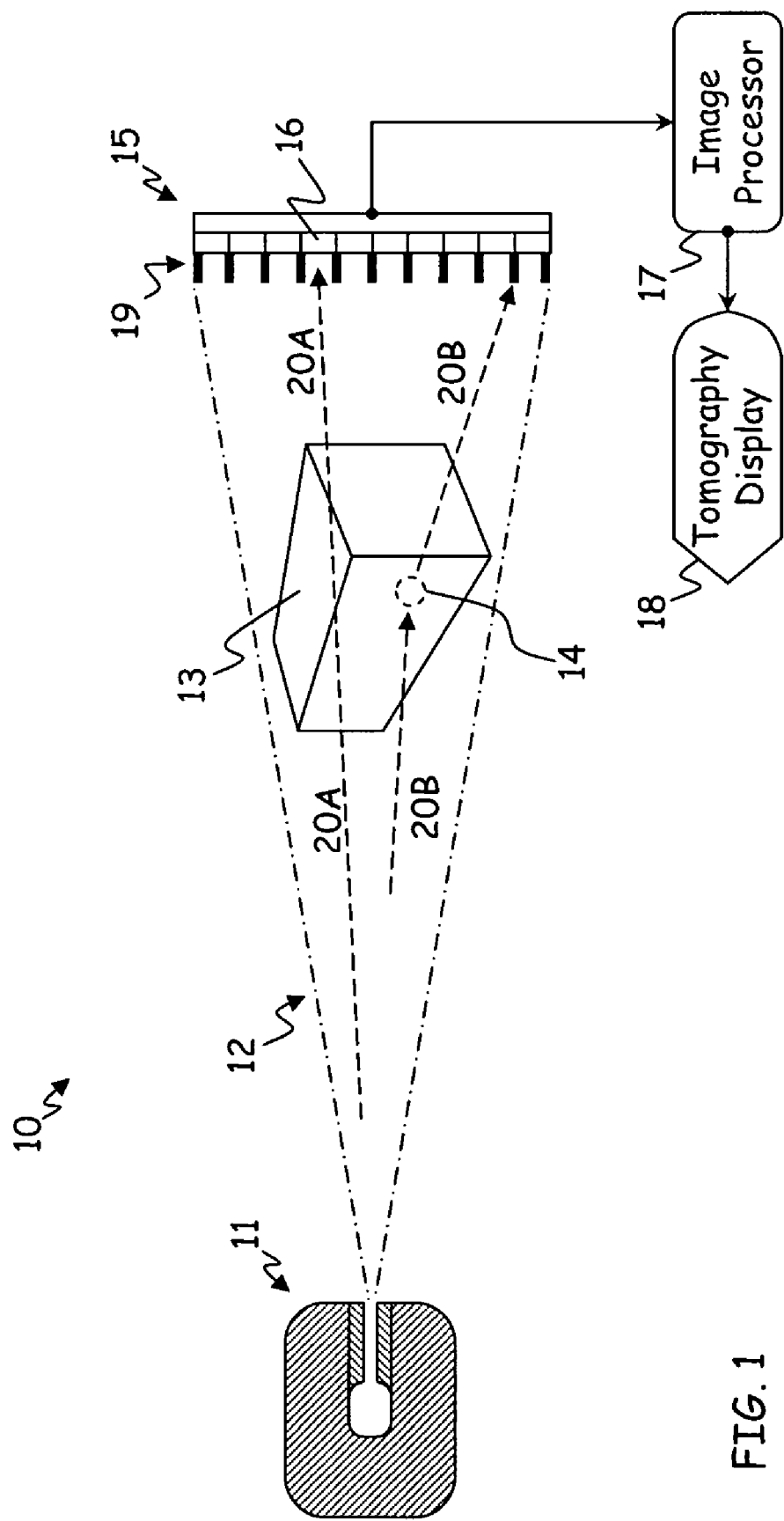
FIG. 1 is a schematic view of a neutron-gamma ray tomography system.

FIG. 1 is a schematic view of neutron-gamma ray tomography system 10. System 10 utilizes neutron-gamma ray source 11 to generate dual neutron-gamma ray beam 12, which illuminates container 13. System 10 interrogates container 13 in order to detect object 14, utilizing fast tomography performed as a function of neutron and gamma ray attenuation, coefficients, which are characterized by detector array 15.

In preferred embodiments, neutron-gamma ray source ("source") 11 is a variable-ratio neutron-gamma ray source comprising a neutron generator, a collimator, and an external gamma target, as described below with respect to FIG. 2A and FIGS. 4A-4C; or source 11 is a dual neutron-gamma ray source comprising a neutron generator, a collimator, and an internal gamma target, as described below with respect to FIG. 2B and FIGS. 3A-3C. Alternatively, source 11 comprises at least one distinct neutron source and at least one distinct gamma ray source, where the distinct sources operate in a coordinated manner to generate dual neutron-gamma ray beam 12.

As shown in FIG. 1, dual beam 12 illuminates container 13 in the direction of detector array 15. In a preferred embodiment, container 13 is an ISO cargo container and object 14 is located inside container 13. In alternate embodiments, tomography system 10 images container 13 independently of any particular object 14, or images object 14 independently of any particular container 13. In these embodiments, container 13 encompasses a range of more generalized forms such as non-ISO cargo containers, motor vehicles, train cars, aircraft, marine vessels, or personal luggage, and object 14 represents a similar range of materials such as hazardous chemicals, improvised explosives, contraband, or special nuclear material (SNM). System 10 is also adaptable to more generalized imaging and detection applications, including medical imaging, forensics, scientific research, and very-large-scale applications in which container 13 represents a building, bridge, or other structure, and object 14 represents an individual engineering element or a construction defect.

Detector array 15 comprises an array of individual detector elements 16, image processor 17, and tomography display 18. In preferred embodiments, detector array 15 also comprises secondary collimator 19.

Depending upon the particular configuration of detector array 15, individual detector elements 16 include, but are not limited to, cryogenic solid state detectors such as high purity germanium (HPGe) detectors or germanium-lithium (GeLi) detectors, room-temperature solid state detectors such as cadmium zinc telluride (CZT) detectors, scintillator detectors such as sodium-iodide (NaI) or thallium-doped sodium iodide NaI(Tl) detectors, and other particle detectors sensitive to neutrons and gamma rays.

Detector elements 16 are arranged in array 15 in order to detect particles (gamma rays and neutrons) from dual beam 12 that are transmitted through container 13 and object 14. Detector array 15 has sufficient resolution to detect neutron and gamma ray transmission independently, and to determine the transmitted flux and intensity for each component. This allows detector array 15 to independently characterize the attenuation of neutrons and gamma rays in container 13 and object 14.

In some embodiments, detector elements 16 are also configured to measure energy spectra for the neutrons and gamma rays. In further embodiments, detector elements 16 additionally provide directional data regarding the individual paths of each particle, allowing detector array 15 to discriminate among particles that are transmitted through container 13, and particles that are scattered from or emitted by object 14.

In some embodiments, secondary collimator 19 is positioned between container 13 and detector elements 16. In these embodiments, secondary collimator 19 is a component of detector array 15, and is distinguished from primary (or "beam") collimators 23A, 23B and 23C of FIGS. 2A, 2B, and 2C, respectively, as described below.

Secondary collimator 19 comprises a number of individual secondary collimator elements, each oriented along the direction of dual beam 12. In these embodiments, transmitted particles (neutrons or gamma rays) 20A pass through secondary collimator 19 directly to detector elements 16, while scattered particles 20B emerge along divergent paths, and are preferentially absorbed or re-scattered by secondary collimator 19. Secondary collimator 19 thus reduces the relative probability that scattered particles 20B (or any other particles not aligned along dual beam 12) reach detector elements 16. This allows image processor 17 to generate higher resolution two-dimensional (2-D) transmission radiographs of container 13 and object 14, independently of any directional data provided by detector elements 16.

Figure 2A:
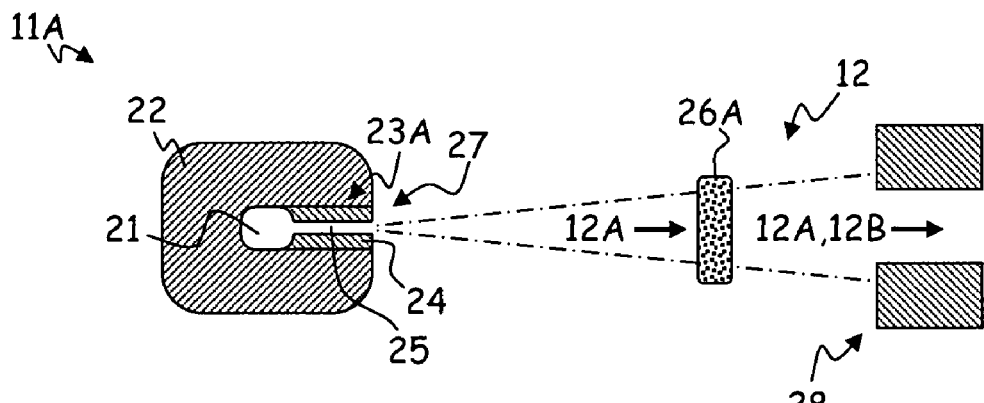
FIG. 2A is a cross-sectional view of a variable-ratio neutron-gamma ray source with an external gamma target.
Figure 2B:
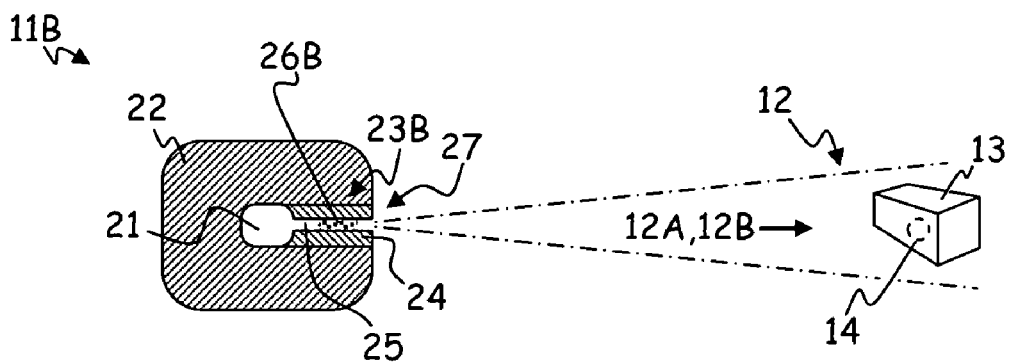
FIG. 2B is a cross-sectional view of a dual neutron-gamma ray source with an internal gamma target.
Figure 2C:
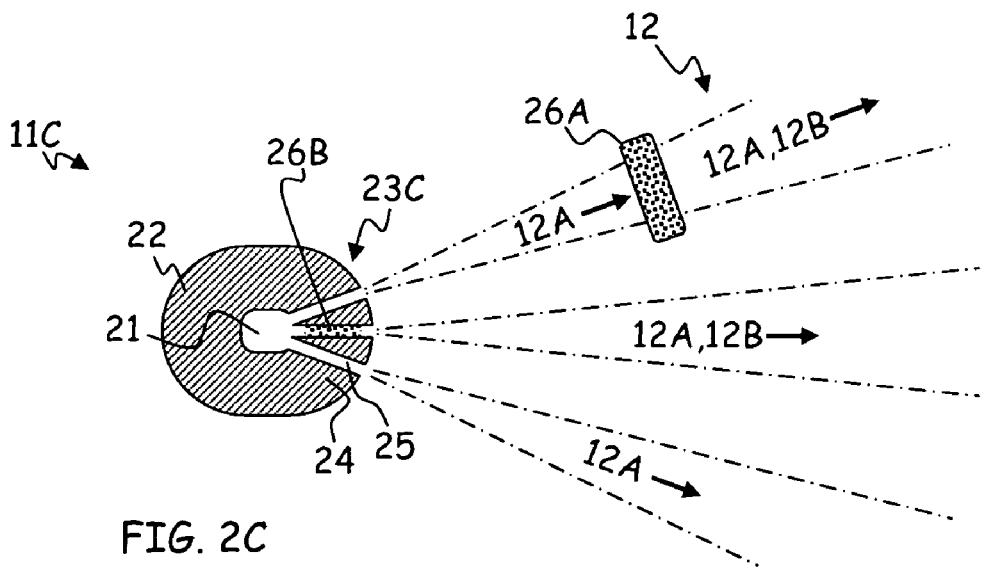
FIG. 2C is a cross-sectional view of a multiple-channel neutron-gamma ray source with a multiple-channel collimator.

Secondary collimator 19 is particularly useful in embodiments where neutron-gamma ray source 11 is a multiple-beam source comprising a combination of individual variable-ratio neutron-gamma ray sources (FIG. 2A) or dual neutron-gamma ray sources (FIGS. 2B and 2C). In these embodiments, source 11 simultaneously illuminates container 13 and object 14 with a plurality of beams 12, each illuminating container 13 toward a different set of detector elements 16 in detector array 15.

In these multiple-beam embodiments, secondary collimator 19 not only suppresses scattered particles but also limits the angular acceptance of each individual detector element 16 to one of beams 12. This allows detector array 15 to characterize neutron and gamma ray attenuation independently for each of the beams, and allows image processor 17 to generate a simultaneous series of 2-D transmission (or "projection") radiography images of container 13 and object 14. This provides faster, more efficient imaging than prior art systems, facilitating a more cost-effective cargo container inspection program.

Image processor 17 is also configured for fast computer-assisted tomography (CAT) and other imaging techniques, which convert the 2-D transmission images into three-dimensional (3-D) tomography. The 2-D transmission images characterize the total thickness (that is, the slant depth, or mass per unit area) of container 13 (and its contents), as projected along beam 12. Fast tomography, in turn, characterizes the 3-D structure of container 13 and object 14.

Because system 10 generates tomography as a function of both neutron and gamma ray attenuation, it provides significant advantages over prior art systems utilizing single-component beams. These advantages include advanced imaging techniques and additional structural and composition analysis, as described below with respect to FIG. 2C.

Typically, fast tomography is generated from the series of simultaneous 2-D transmission images, as provided by multiple beams 12 and detector array 15 with secondary collimator 19. In embodiments where detector elements 16 provide angular data, however, fast tomography is also generated from individual beams 12 and individual 2-D transmission images, by utilizing the directional data to discriminate among scattered, transmitted, and emitted particles, independently of secondary collimator 19. Further, in embodiments where detector elements 16 measure energy spectra, system 10 provides additional image resolution and materials detection capability via gamma ray spectroscopy (including prompt gamma activation analysis, or PGAA) or neutron-activated spectroscopy (including neutron activation analysis, or NAA).

FIG. 2A is a cross-sectional view of variable-ratio neutron-gamma ray source 11A. Variable-ratio source 11A comprises neutron generator 21, shield 22, primary collimator 23A with collimator walls 24 and channel 25, and external gamma target 26A positioned outside collimator channel 25, downstream of collimator port 27 and outside of shield 22.

In an exemplary embodiment, neutron generator 21 is compact neutron generator (CNG) generating a substantially monochromatic 14.1 MeV (approximately 14 MeV) neutron flux of up to $3.5 \times 10^{14}$ n/s (350 trillion neutrons per second), via a deuterium-tritium (D-T) fusion process initiated by a deuterium ion plasma incident on a tritium-hydrated (tritiated) titanium/aluminum (Ti/Al) fusion target matrix. Alternatively, the fusion target matrix is deuterated and the plasma is a tritium plasma.

In other embodiments, CNG 21 utilizes a deuterium plasma and a deuterated fusion target matrix to generate a D-D (deuterium-deuterium) neutron flux of up to $3.5 \times 10^{12}$ n/s (3.5 trillion neutrons per second) with a characteristic energy of 2.45 MeV (approximately 2.5 MeV). In further embodiments, the plasma is a tritium plasma and the fusion target matrix is tritiated. In these embodiments, CNG 21 generates a tritium-tritium (T-T) neutron flux with a substantially distributed energy spectrum, rather than a substantially monochromatic energy spectrum.

In a preferred embodiment, CNG 21 is a single-fusion-target coaxial neutron generator with dimensions of approximately thirty centimeters or less in diameter, and approximately thirty centimeters or less in length. This embodiment is, however, merely representative. For higher-intensity applications, the dimensions are larger to accommodate a coaxially nested fusion-target configuration in which multiple ion plasmas impinge on both sides of a number of fusion target matrices. In these embodiments, the neutron flux is enhanced by a factor of up to ten or more. In lower-intensity applications, the dimensions of CNG 21 are sometimes smaller, and the neutron flux is reduced by a factor of up to one million or more. Alternatively, neutron generator 21 is not a CNG, but an alternate neutron generator such as an isotopic neutron generator comprising a californium (Ca), americium-beryllium (Am—Be), plutonium-beryllium (Pu—Be) or radium-beryllium (Ra—Be) source, or a fission reactor.

Shield 22 surrounds neutron generator 21 to reduce external radiation exposure. In one embodiment, shield 22 comprises a dense shield material including, but not limited to, steel, lead, tungsten, iron, concrete, or depleted uranium. In these embodiments, shield 22 is up to seventy-five centimeters (75 cm) thick, or more.

In other embodiments, shield 22 comprises a neutron moderator such as water (either heavy water, $D_2O$, or light water, $H_2O$), or a light hydrocarbon such as paraffin. In these embodiments, energetic neutrons from neutron generator 21 undergo multiple scattering in shield 22, and are converted to thermal neutrons characterized by an average thermal energy. Shields comprising neutron moderators are typically surrounded by a layer of material with a high cross section for thermal neutron capture, such as hafnium (Hf), cadmium (Cd), or boron carbide ($B_4C$). In further embodiments, shield 22 is a composite shield, comprising a combination of dense shield materials, neutron moderators, or materials with a high cross section for thermal neutron capture.

Collimator 23A comprises collimator walls 24 and collimator channel 25, which traverses shield 22 from neutron generator 21 to port 27. In a preferred embodiment, collimator channel 25 extends from neutron generator 21 through shield 22, such that port 27 is located on an external surface of shield 22. In alternate embodiments, port 27 is recessed within the shield 22, or extends beyond the external surface of shield 22.

Collimator walls 24 are typically comprised of a shield material, as described above for shield 22. In one embodiment, collimator walls 24 are integrally formed with shield 22. In other embodiments, collimator walls 24 are formed independently of shield 22, and configured so that the collimator is removable and interchangeable with other collimator configurations.

Collimator 23A is a primary collimator or "beam collimator" for neutron beam 12A. Whereas neutrons from generator 21 preferentially interact in shield 22, and do not reach the exterior surface of shield 22, neutrons from generator 21 preferentially pass through collimator channel 25 to port 27, producing collimated neutron beam 12A. In the external gamma target configuration of collimator 23A, neutron beam 12A impinges on external gamma target 26A, undergoing inelastic scattering to generate dual neutron-gamma ray beam 12 with neutron component 12A and gamma component 12B.

The gamma target (either external gamma target 26A, as shown here, or internal gamma target 26B, as shown in FIG. 2B) typically comprises a material with a substantial cross section for inelastic neutron scattering. In one embodiment, for example, the gamma target comprises graphite or another form of carbon (C), with an inelastic scattering threshold of about 4.9 MeV.

In this embodiment, neutrons with a characteristic energy of approximately 14 MeV undergo inelastic scattering in the gamma target to produce gamma rays with a characteristic energy of 4.43 MeV (approximately 4.4 MeV). For 14 MeV neutrons incident on graphite, a gamma target thickness of approximately 7.5-8.0 cm generates dual neutron-gamma ray beam 12 with approximately a two-to-one flux ratio of neutrons to gamma rays (that is, a neutron-gamma ratio approximating 2:1).

In another embodiment, the gamma target comprises aluminum (Al). In this embodiment, neutrons with a characteristic energy of approximately 2.5 MeV undergo inelastic scattering to produce 1.0 MeV gamma rays. Gamma targets also have composite embodiments. Some composite gamma targets comprise a variety of different gamma target materials, and other composite gamma targets comprise a neutron moderator such as paraffin or water, which lowers the average neutron energy and converts substantially monochromatic neutron spectra to continuous neutron spectra. Further composite gamma targets comprise neutron multipliers such as lithium (Li), beryllium (Be) or lead (Pb), which lower the average neutron energy and increase the neutron flux. More generally, both external gamma targets 26A and internal gamma targets 26B (as shown in FIG. 2B) comprise a wide range of different gamma/secondary particle target compositions, including, but not limited to, gamma target materials, neutron moderators, and neutron multipliers.

Beam 12 takes on a variety of geometries including conical, rectangular, trapezoidal, and fan-shaped forms, each with a diverging beam profile that depends upon the geometry of the primary collimator, particularly the width of channel 25 and the cross-sectional profile of port 27. Dual beam 12 is thus not an ideal linear beam, but diverges from port 27 to encompass a continuous range of beam angles. In some embodiments, this range is reduced by downstream collimator 28, positioned downstream of the gamma/secondary particle target.

FIG. 2B is a cross-sectional view of dual neutron-gamma ray source 11B, with internal gamma target 26B. Dual source 11B comprises neutron generator 21, shield 22 and primary collimator 23B, with internal gamma target 26B positioned inside collimator channel 25, upstream of collimator port 27 and within shield 22. This distinguishes from collimator 23A of FIG. 2A, above, in which external gamma target 26A is positioned downstream of collimator port 27, outside collimator channel 25 and shield 22.

In the internal gamma target embodiment shown here, neutron beam 12A is incident on internal gamma target 26B within collimator channel 25, such that dual beam 12 emerges from port 27 with both neutron component 12A and gamma component 12B. This offers advantages in size of the source and simplicity of design.

In both internal and external gamma target configurations, dual beam 12 has sufficient intensity to interrogate container 13 and detect object 14. The neutron and gamma components 12A and 12B each illuminate container 13 with sufficient intensity and penetration to generate 2-D transmission radiography characterizing the interior of container 13, and 3-D tomography characterizing the structure object 14. Beam 12 is further configurable to simultaneously illuminate the entirety of container 13, or to illuminate substantial portions of container 13. In these latter partial-illumination configurations, beam 12 is typically swept over container 13 via rotational or translational motion of the source, or, equivalently, via rotational or translational motion of container 13.

FIG. 2C is a cross-sectional view of multiple-channel neutron-gamma ray source 11C with multiple-channel collimator 23C. Multiple-channel source 11C comprises neutron generator 21, shield 22 and multiple-channel collimator 23C, where collimator 23C has a plurality of individual collimator channels 25.

The number of collimator channels 25 in FIG. 2C is three, but this is merely representative. In other embodiments there are one, two, four or more collimator channels 25. Typically, the channels are oriented such that beams 12 emerge in a number of different directions, providing more cost-effective and efficient utilization of neutron generator 21, and greater illumination for faster tomography. Preferentially, individual collimator channels 25 of multiple-channel collimator 23C have collimator walls 24 configured within interchangeable collimators 23A (with external gamma targets) or interchangeable collimators 23B (with internal gamma targets), as described above, such that beam or beams 12 can be adapted or "tuned" to different imaging and detection applications.

The energy spectrum of neutron generator 21 and the thickness of the gamma targets (in units of mass per area along beam 12A) determine the intensity, neutron-gamma ratio, and energy spectra of dual beams 12. In composite gamma/secondary particle embodiments, neutron moderators and neutron multipliers also affect the properties of the beams, as discussed above with respect to FIG. 2A. The beam properties are thus adaptable to a range of imaging applications, including small-scale, sensitive applications such as medical imaging, for which the intensity and energy spectra will typically be lower, and large-scale, high-speed applications such as cargo container interrogation, for which the intensity and energy spectra will typically be higher.

In some embodiments, the gamma target configuration varies from collimator channel to collimator channel. In particular, some individual beams 12 have a relatively thick gamma target, such that most neutrons undergo inelastic scattering and the neutron-gamma ratio is relatively low. Other individual beams 12 have a relatively thin gamma target, such that fewer neutrons undergo inelastic scattering and the neutron-gamma ratio is relatively high. Variations in gamma target configuration also encompass composite gamma/secondary particle target compositions, such that the neutron and gamma ray components of beams 12 vary not only in beam angle and neutron-gamma ratio, but also in intensity and energy spectra.

In alternate embodiments, the gamma target configuration is substantially uniform from collimator to collimator. In these embodiments, individual beams 12 differ primarily in beam angle, not other beam properties (intensity, neutron-gamma ratio and energy spectra).

Figure 3A:
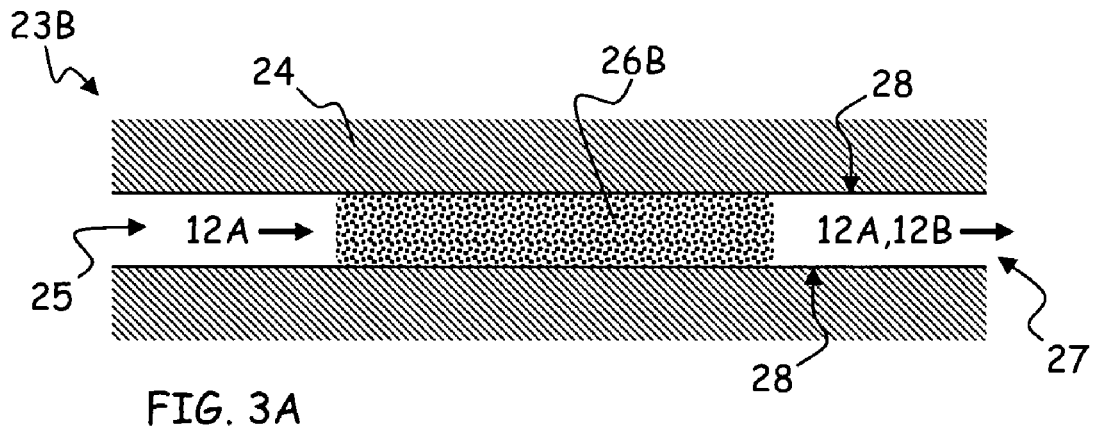
FIG. 3A is a cross-sectional view of a primary collimator for a dual neutron-gamma ray source, in a linear embodiment.
Figure 3B:
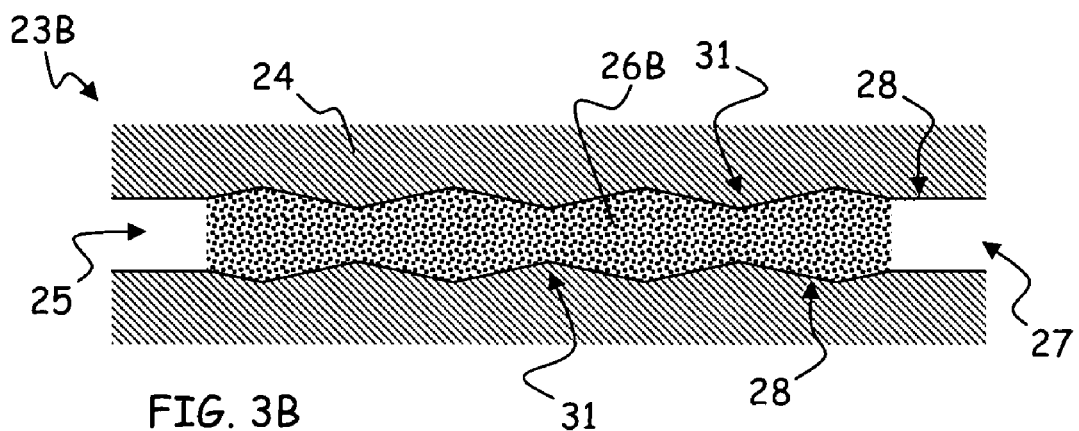
FIG. 3B is a cross-sectional view showing the primary collimator of FIG. 3A, in a feathered embodiment.
Figure 3C:
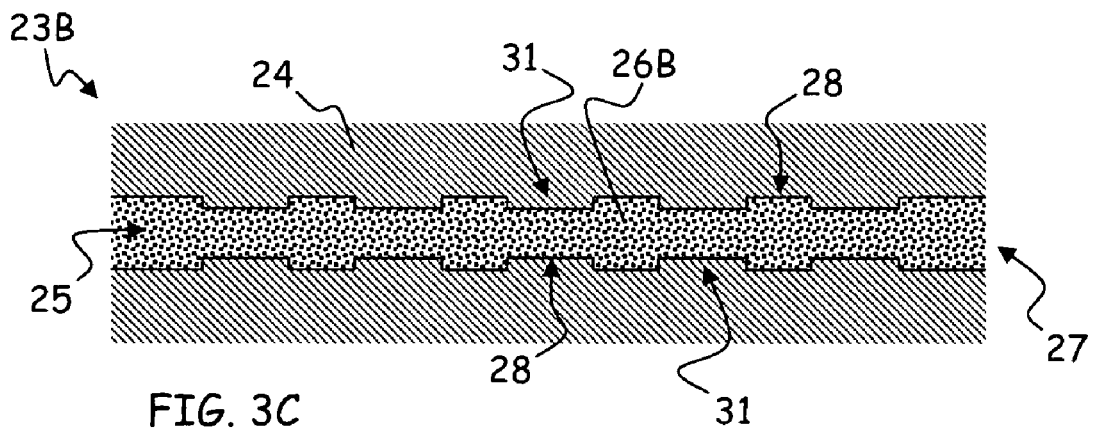
FIG. 3C is a cross-sectional view showing the primary collimator of FIG. 3A, in an alternate feathered embodiment.

Note that FIG. 3C encompasses embodiments in which the gamma target is absent from one or more beam paths. Typically, these beam paths will still have a residual gamma ray component, due to background gamma rays generated in collimator walls 24 and shield 22. As FIG. 3 illustrates, however, at least one collimator channel has a substantial thickness of gamma target, such that the source generates at least one dual beam 12 with neutron component 12A and gamma ray component 12B, where gamma ray component 12B is due to inelastic scattering of neutron component 12A from the gamma target, and not due to background.

In the particular embodiment of FIG. 2C, multiple-channel neutron-gamma ray source 11C comprises both external gamma targets 26A and internal gamma targets 26B. In these embodiments, neutron-gamma source 11C is a dual, variable-ratio neutron-gamma ray source, combining the advantages of collimators 23A, with external gamma targets 26A (as shown in FIG. 2A), and collimators 23B, with internal gamma targets 26B (as shown in FIG. 2B).

FIG. 2C further illustrates that the external structure of shield 22 is adaptable to a variety of neutron generator, collimator channel, and gamma target configurations. In particular, shield 22 encompasses both oblong rectangular configurations (as shown in FIGS. 2A and 2B) and substantially oval configurations (as shown in FIG. 2C), as well as generally cylindrical configurations and other shield geometries.

After emerging from the neutron-gamma ray source (variable-ratio source 11A, dual source 11B, or multiple-channel source 11C, or an alternate neutron-gamma ray source), each dual neutron-gamma ray beam 12 illuminates an object of interest. Equivalently, each beam 12 interrogates a container that either contains an object of interest, or is itself an object of interest. Some particles in beam 12 scatter or are absorbed, resulting in attenuation within the object, and others do not interact, producing transmission through the object. Attenuation in the beam reduces the transmitted intensity. This allows the detector array to characterize the object's structure and composition, particularly its slant depth along the beam, via 2-D transmission radiography and 3-D tomography as described above. In contrast to the prior art, however, dual beam 12 comprises both neutrons (beam component 12A) and gammas (beam component 12B), providing for richer structural imaging and more advanced composition analysis.

One way to characterize this advantage is the neutron-gamma attenuation ratio. The attenuation ratio (R) is the ratio of neutron and gamma ray attenuation coefficients; that is, $$R \equiv \frac{\mu_n}{\mu_\gamma}, \quad [2]$$

where $\mu_n$ and $\mu_\gamma$ are the mass attenuation coefficients for neutrons and gamma rays, respectively. The attenuation coefficients are defined by the natural logarithm (ln) of the ratio of attenuated beam intensity I (after transmission through the object) to unattenuated intensity $I^0$ (before transmission), as determined independently for neutrons ($I_n$) and gamma rays ($I_\gamma$). Thus $$\mu_n = \ln(I_n/I_n^0), \text{ and} \quad [3]$$

$$\mu_\gamma = \ln(I_\gamma/I_\gamma^0). \quad [4]$$

The neutron-gamma attenuation ratio discriminates among different material compositions. In embodiments where the neutron-gamma ray source generates 14 MeV neutrons and 4.4 MeV gamma rays, for example, the attenuation ratio varies from over five for light materials such as hydrogen and helium, to approximately one for iron, and to less than one-half for uranium, plutonium, and other transuranic elements.

The attenuation ratio varies because the neutron component (12A) of dual beam 12 interacts predominantly via the strong nuclear force, which depends upon atomic mass A, while the gamma ray component (12B) interacts predominantly via the electromagnetic force, which depends upon the square of the atomic number ($Z^2$). While both neutrons 12A and gamma rays 12B characterize density along the beam path, therefore, the attenuation ratio provides an additional analysis tool, independent of either the neutron or gamma ray attenuation coefficient alone.

The attenuation ratio has particular discriminating power among objects with the same slant depth (mass per unit area along the beam), but different material compositions, as characterized by the ratio of atomic mass to atomic number squared ($A/Z^2$). The attenuation ratio is capable of distinguishing, for example, between a solid aluminum object, and a higher-density strategic nuclear material with the same size and shape, but which has been hollowed out yield the same total mass.

FIG. 3A is cross-sectional view of primary collimator 23B for a dual neutron-gamma ray source, in a linear embodiment. Collimator 23B comprises collimator walls 24, forming collimator channel 25 with internal gamma target 26B, and port 27.

Regardless of gamma target configuration, collimator channel 25 is characterized by an elongated geometry that defines a range of beam angles from the neutron generator (not shown) to collimator port 27. In the particular embodiment of FIG. 3A, the collimator is also linear, with collimator walls 24 substantially parallel along collimator channel 25, and interfaces 28 extending substantially linearly to collimator port 27.

FIG. 3B is a cross-sectional view of primary collimator 23B in a feathered embodiment. In this embodiment, interfaces 28 between collimator walls 24 and channel 25 are not linear, and walls 24 are not parallel along collimator 23B. Instead, interfaces 28 and collimator walls 24 comprise non-linear "zigzag" or feathered regions 31.

This contrasts with the linear embodiment of FIG. 3A, which has the advantage of simpler design but also permits "streaming" of neutrons along interfaces 28, between internal gamma target 26B and collimator walls 24. Streaming poses a substantial problem for high-intensity neutron generators, for which even a very narrow gap can result in a significant streaming flux.

Feathered regions 31 prevent neutron streaming by eliminating straight-line paths along interfaces 28, requiring each neutron to pass through either collimator walls 24 or internal gamma/secondary particle target 26B. Feathering improves beam uniformity by eliminating streaming components that have anomalous properties with respect to the rest of the beam, such as a different range of beam angles, different intensity, different neutron-gamma ratio or different energy spectra. This provides greater beam uniformity, which enhances imaging by improving structural resolution and increasing discrimination among different material compositions.

In some embodiments, both collimator walls 24 and internal gamma target 26B comprise a shield material, such that the particle intensity at port 27 is substantially reduced. In these embodiments, collimator 23B "plugs" the port by shutting off the beam, reducing intensity at port 27 to a level approaching the isotropic flux just outside the shield, away from port 27. For such a "plug" collimator, feathering substantially reduces the potential for accidental exposure to streaming neutrons.

FIG. 3C is a cross-sectional view of primary beam collimator 23B in an alternate feathered embodiment. In this embodiment, feathered regions 31 are castellated or "toothed," but otherwise have a similar effect to the "zigzag" feathering configuration of FIG. 3B.

Together, FIGS. 3B and 3C are illustrative of a wide range of feathered collimator embodiments. These include piecewise-linear configurations (as shown), which comprise a combination of feathered regions (with non-parallel walls 24) and non-feathered regions (with parallel walls 24), as well as configurations with curved collimator walls 24, and other, more generalized feathering geometries. FIG. 3C also illustrates that in different embodiments internal gamma/secondary particle target 26B variously fills all, some or none of collimator channel 25 (compare to FIG. 2A).

Figure 4A:
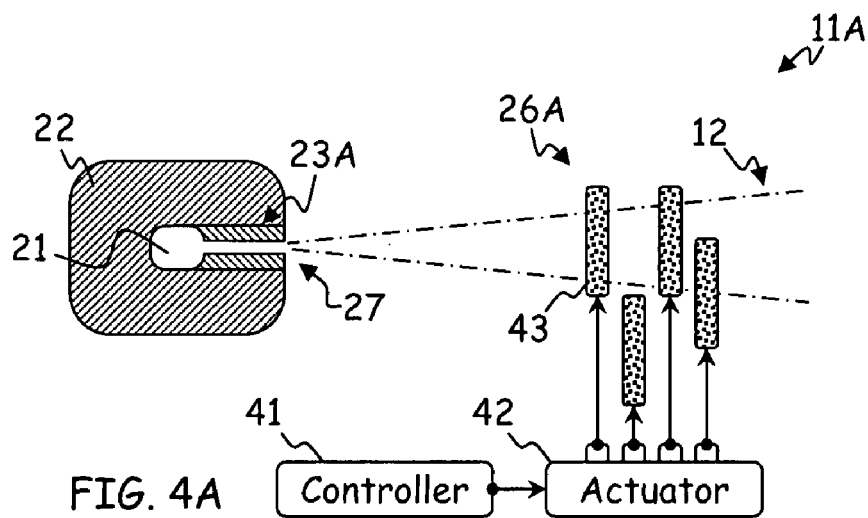
FIG. 4A is a schematic view showing a variable-ratio neutron-gamma ray source, in an embodiment with a multiple-plate external gamma target.

FIG. 4A is a schematic view of variable-ratio neutron-gamma ray source 11A, in an embodiment with multiple-plate external gamma target 26A. In this embodiment, external gamma target 26A comprises controller 41, actuator 42 and plurality of gamma target plates 43.

The thickness and composition of each target plate 43 is independent of the thickness and composition of the others, and each target plate 43 is independently positioned with respect to beam 12 by controller 41 and actuator 42. In one embodiment, actuator 42 comprises a series of linear screw drive mechanisms, hydraulic lift actuators, or other drive mechanisms configured to automatically position plates 43, as determined by drive controller 41. Alternatively, controller 41 represents a human operator, and actuator 42 facilitates manual positioning of target plates 43.

Target plates 43 allow real-time "tuning" of beam 12. As the gamma target thickness (mass per unit area) along beam 12 increases, more gamma rays are produced and the neutron-gamma ratio decreases. As the thickness decreases, the neutron-gamma ratio increases. Independently positioned gamma/secondary particles target plates 43 also vary the intensity and energy spectra of beam 12, in order to accommodate objects and containers with a wide range of densities and compositions, and to enhance imaging at particular slant depths within a given object or container.

Figure 4B:
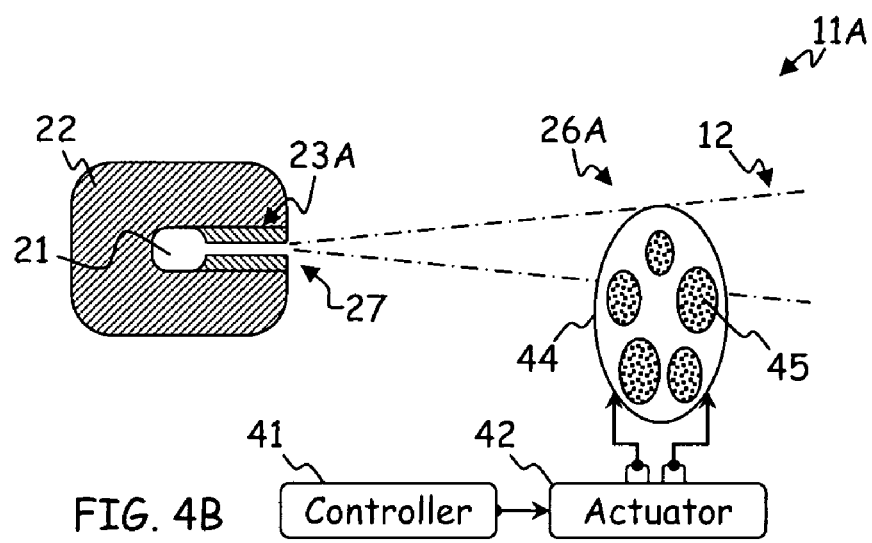
FIG. 4B is a schematic view showing the variable-ratio source of FIG. 4A, in an alternate embodiment with a rotary wheel external gamma target.

FIG. 4B is a schematic view of variable-ratio neutron-gamma ray source 11A, in an alternate embodiment with rotary wheel external gamma target 26A. In this embodiment, external gamma target 26A comprises controller 41, actuator 42, rotary wheel 44, and rotary gamma targets 45.

In contrast to the multiple plate gamma target embodiment of FIG. 4A, rotary targets 45 are typically interchanged, rather than positioned in different combinations, and actuator 42 typically comprises a rotary device such as a stepper motor, rather than a linear actuator. In other respects, rotary gamma targets 45 function analogously to target plates, allowing controller 41 and actuator 42 to tune the neutron-gamma ratio and energy spectra of dual beam 12.

In various embodiments the number of rotary gamma targets 45 varies, from at least two to three, four, five (as shown in FIG. 4B), or more. Alternatively, rotary wheel 44 comprises an integrated rotary target 45, in which the thickness or composition varies as a continuous function of angular position.

Figure 4C:
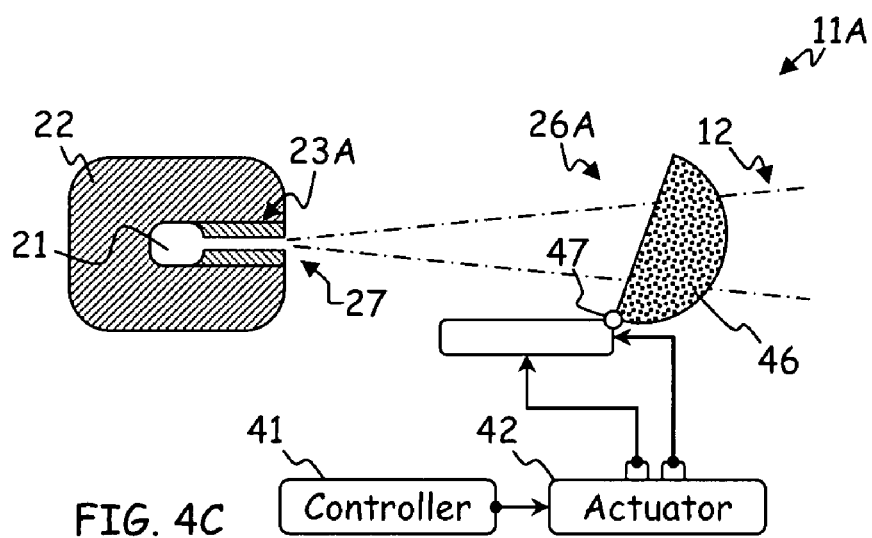
FIG. 4C is a schematic view showing the variable-ratio source of FIG. 4A, in another alternate embodiment with a half-cylindrical drum external gamma target.

FIG. 4C is a schematic view of variable-ratio neutron-gamma ray source 11A, in another alternate embodiment with half-cylindrical drum external gamma target 26A. In this embodiment, external gamma target 26A comprises half-cylindrical drum target 46, which rotates or pivots about hinge (pivot point) 47, tuning the characteristics of beam 12 as a function of the thickness and composition of drum 46 along beam 12.

Typically, drum target 46 is a monolithic structure comprising a uniform composition of graphite, aluminum, or other gamma target material. Alternatively, drum target 46 has a non-uniform composition, and/or comprises a combination of gamma target materials, neutron moderators and neutron multipliers.

As with the embodiments of FIGS. 4A and 4B, drum target 46 is either automatically or manually positioned via controller 41 and actuator/drive mechanism 42. taken together, FIGS. 4A-4C illustrates that actuator 42 is in general configurable for both "discrete" positions, in which one or more external gamma target components (plate targets 43, rotary targets 45, or drum target 46) are positioned entirely within beam 12, or entirely outside of beam 12; and continuous or "intermediate" positions, in which one or more external target components are positioned partly within and partly outside of beam 12. Moreover, controller 41 and actuator 42 are also generally configurable for both rotational and linear motion, such that the thickness and composition of the external gamma target within beam 12 is a function of both linear and rotational position.

Figure 5:
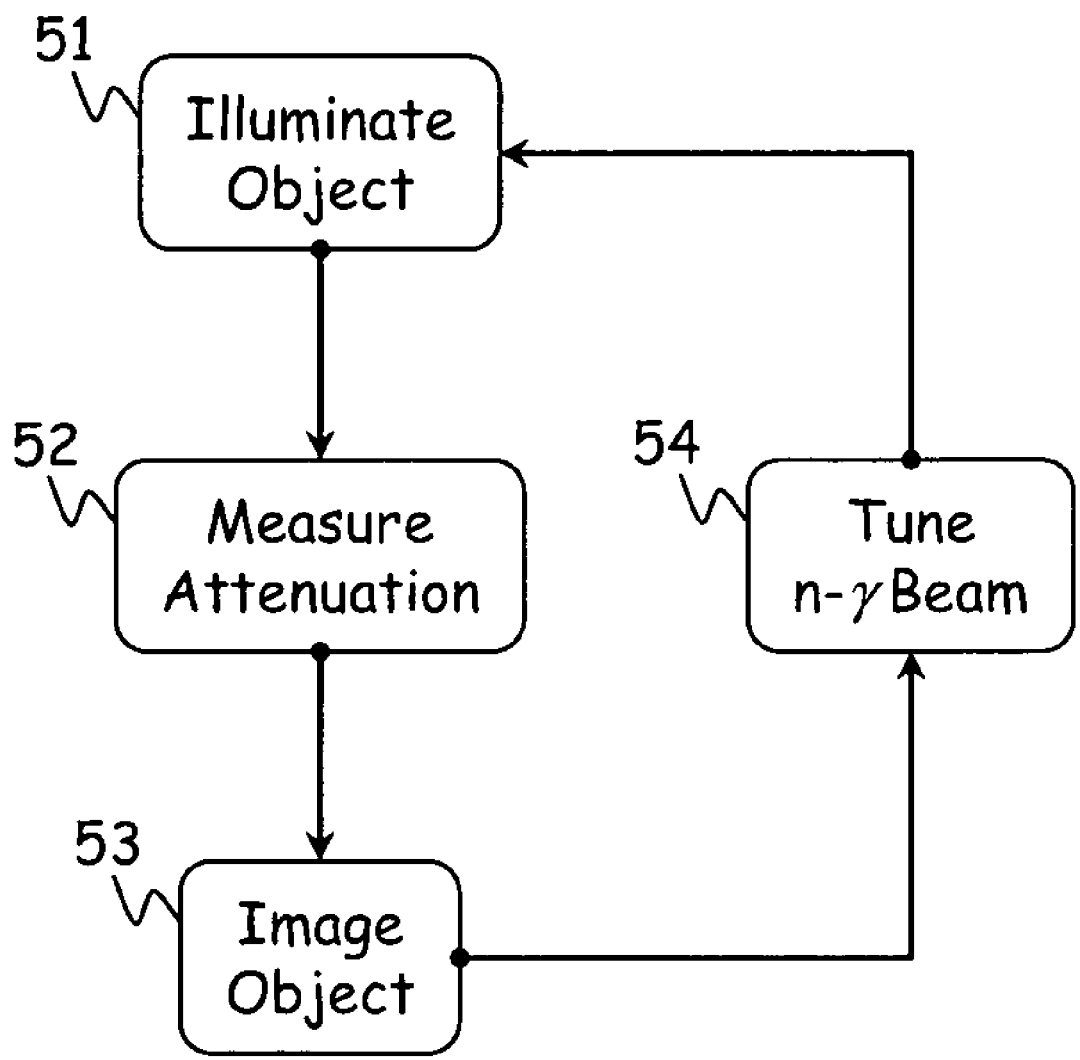
FIG. 5 is a block diagram illustrating a method for neutron-gamma ray tomography.

FIG. 5 is a block diagram illustrating method 50 for neutron-gamma ray tomography. Method 50 comprises illuminating an object with a dual neutron-gamma ray beam (step 51), measuring neutron and gamma ray attenuation (step 52), imaging the object via fast tomography (step 53), and tuning the beam (step 54) to enhance imaging.

Illuminating an object (step 51) comprises generating a dual neutron-gamma ray beam, which is directed through the object toward a detector array. In exemplary embodiments, illuminating the object comprises simultaneously interrogating an ISO shipping container with a plurality of high-intensity, high-energy beams oriented along different beam paths, but method 50 is also adaptable to luggage inspection, medical and forensic imaging, scientific research, structural inspection and other imaging applications, utilizing one or more beams of either higher or lower energy and intensity.

Measuring neutron and gamma ray attenuation (step 52) comprises characterizing neutron and gamma ray attenuation coefficients with a detector array, where the detector array is formed from a plurality of individual detector elements. In a preferred embodiment, secondary collimators limit the angular acceptance of the each individual detector element to one of a plurality of beams. In some embodiments, the detector array measures angular data and energy spectra in addition to the attenuation coefficients.

Imaging the object (step 53) comprises analyzing its structure and composition. A signal processor generates a 2-D projection image (transmission radiography) of the object, as a function of neutron and gamma ray attenuation, and generates a 3-D image (tomography) of the object, as a function of the 2-D projection. The signal processor further, analyzes the composition of the object, also as a function of attenuation. In a preferred embodiment, the function of attenuation comprises independent neutron and gamma ray attenuation coefficients. In a further preferred embodiment, the function comprises a neutron-gamma attenuation ratio.

Imaging (step 53) combines computerized pattern recognition algorithms and human operator interpretation of 2-D transmission images and 3-D tomography images, which are typically enhanced by color coding indicative of the neutron-gamma ratio. This allows method 50 to discriminate among objects that have similar structures and slant depths, but are comprised of different materials. Specifically, imaging allows the detector array to detect objects with an anomalous density or an anomalous ratio of atomic mass to atomic number squared ($A/Z^2$), including special nuclear materials. Imaging also discriminates among SNM and other high-density materials such as shielding, and among lower-density materials such as conventional explosives or electronic components.

In some embodiments, imaging also comprises prompt gamma activation analysis (PGAA) or other gamma ray spectroscopy, or neutron activation analysis (NAA) or other neutron-activated spectroscopy. Note that PGAA and NAA methods contrast with prior art passive detection systems, because the induced signals are a function of beam intensity, and are thus generated at high intensity. In particular, this allows system 50 to defeat shielding designed for prior art passive detection systems, which are based on lower-level natural radioactive decay.

Tuning the beam (step 54) comprises varying its intensity, neutron-gamma ratio, or energy spectra by changing the thickness or composition of a gamma target. In preferred embodiments, method 50 is performed iteratively, such that tuning continually enhances structural resolution and continually improves discrimination among different material compositions. In these embodiments, tuning is typically accomplished by positioning an external gamma/secondary particle target in real time, as described with respect to FIGS. 4A-4C, above. In alternate embodiments, tuning comprises interchanging primary collimators with internal gamma/secondary particle targets, as described with respect to FIGS. 3A-3C.

Tuning the beam enhances the advantages of method 50, providing a level of discrimination unavailable in prior art systems that do not utilize dual-component neutron-gamma ray beams, are not configured to generate 3-D tomography, and cannot vary beam properties including intensity, neutron-gamma ratio, and energy spectra.

Although the present invention has been described with reference to preferred embodiments, the terminology used is for the purposes of description, not limitation. Workers skilled in the art will recognize that changes may be made in form and detail without departing from the spirit and scope of the invention.

The invention claimed is:

1. A neutron-gamma ray tomography system comprising:
   a source for illuminating an object with a dual neutron-gamma ray beam, the source comprising a gamma target having a variable thickness, wherein the dual neutron-gamma ray beam has a variable neutron-gamma ratio as a function of the variable thickness;
   a detector array for characterizing neutron and gamma ray attenuation in the object; and
   an image processor for generating tomography as a function of the neutron and gamma ray attenuation.

2. The system of claim 1, wherein the source generates neutrons via a fusion process comprising at least one of deuterium-deuterium, deuterium-tritium, or tritium-tritium fusion reactions, and further generates gamma rays via inelastic scattering of the neutrons from the gamma target.

3. The system of claim 1, wherein the source simultaneously illuminates the object with a plurality of dual neutron-gamma ray beams.

4. The system of claim 3, wherein the gamma target comprises a neutron moderator or a neutron multiplier.

5. The system of claim 1, wherein the detector array comprises a cryogenic solid state detector element.

6. The system of claim 1, wherein the detector array comprises a room-temperature solid state detector element.

7. The system of claim 1, wherein the detector array comprises a scintillation detector element.

8. A neutron-gamma ray tomography system comprising:
   a source for illuminating an object with a dual neutron-gamma ray beam;
   a detector array for characterizing neutron and gamma ray attenuation in the object; and
   an image processor for generating tomography as a function of the neutron and gamma ray attenuation;
   wherein the function of the neutron and gamma ray attenuation comprises a neutron-gamma attenuation ratio.

9. The system of claim 8, wherein the image processor further analyzes material composition as a function of the neutron-gamma attenuation ratio.

10. The system of claim 8, wherein the image processor further analyzes material composition as a function of at least one of gamma ray spectroscopy or neutron-activated spectroscopy.

11. A container interrogation system comprising:
    a source for interrogating the container with a dual neutron-gamma ray beam;
    a detector array for detecting neutron and gamma ray transmission through the container; and
    an image processor for generating three-dimensional tomography as a function of the neutron and gamma ray transmission, wherein the function of the neutron and gamma ray attenuation comprises a neutron-gamma attenuation ratio.

12. The system of claim 11, wherein the container has a total length of at least three meters and a capacity of at least ten thousand kilograms.

13. The system of claim 11, wherein the three-dimensional tomography comprises an image of an object in the container.

14. The system of claim 13, wherein the image is enhanced by varying at least one of an intensity, a neutron-gamma ratio, or an energy spectrum of the dual neutron-gamma ray beam.

15. A method for neutron-gamma ray tomography, the method comprising:
    illuminating an object with a plurality of dual neutron-gamma ray beams;
    measuring a neutron-gamma ray attenuation ratio for each of the dual neutron-gamma ray beams;
    imaging the object via tomography performed as a function of the neutron and gamma ray attenuation ratio; and
    tuning the beam to enhance the tomography.

16. The method of claim 15, wherein tuning the beam comprises varying at least one of an intensity, a gamma ray intensity, or an energy spectrum.

17. The method of claim 15, wherein imaging the object further comprises analyzing a material composition of the object as a function of the neutron-gamma attenuation ratio.

18. The method of claim 17, wherein analyzing a material composition further comprises at least one of prompt gamma activation analysis or neutron activation analysis.

\* \* \* \* \*